(12) United States Patent
Zaltman

(10) Patent No.: US 6,315,569 B1
(45) Date of Patent: Nov. 13, 2001

(54) METAPHOR ELICITATION TECHNIQUE WITH PHYSIOLOGICAL FUNCTION MONITORING

(75) Inventor: Gerald Zaltman, Harvard University, Graduate School of Business Administration, Morgan Hall 190, Soldiers, Field Rd., Boston, MA (US) 02163

(73) Assignee: Gerald Zaltman

( * ) Notice: Subject to any disclaimer, the term of this patent is extended or adjusted under 35 U.S.C. 154(b) by 0 days.

(21) Appl. No.: 09/028,382

(22) Filed: Feb. 24, 1998

(51) Int. Cl.[7] ................................................. G09B 19/00
(52) U.S. Cl. ..................... 434/236; 434/323; 434/322; 434/362; 600/301; 600/306; 707/530
(58) Field of Search .................................. 434/236, 238, 434/258, 362, 322, 323; 706/927, 45, 15, 16; 705/1, 2, 11; 707/500, 530; 600/301, 306

(56) References Cited

U.S. PATENT DOCUMENTS

| | | | |
|---|---|---|---|
| 5,243,517 | * 9/1993 | Scmidt et al. | 434/236 X |
| 5,253,168 | * 10/1993 | Berg | 364/413.01 X |
| 5,436,830 | * 7/1995 | Zaltman | 707/530 |
| 5,613,498 | * 3/1997 | Yasushi et al. | 128/731 X |

* cited by examiner

Primary Examiner—Valencia Martin-Wallace
Assistant Examiner—Chandra Harris
(74) Attorney, Agent, or Firm—Roberts Abokhair & Mardula, LLC

(57) ABSTRACT

A process and apparatus for using a metaphor elicitation technique in conjunction with physiological function monitoring to elicit, organize and analyze data pertaining to a research topic. The metaphor elicitation technique process and apparatus is improved with the acquisition of data related to a user's physiological functioning. This data provides further insight and understanding which can be used in creating an appropriate marketing campaign for a product, improving inter-office communications and determining the presence of pre-existing biases or beliefs.

22 Claims, 2 Drawing Sheets

METAPHOR ELICITATION TECHNIQUE WITH PHYSIOLOGICAL FUNCTION MONITORING

FIELD OF THE INVENTION

This invention relates to an improved marketing research tool. Specifically, it relates to using a metaphor elicitation technique in conjunction with physiological function monitoring to determine a consumer's response to marketing input.

BACKGROUND OF THE INVENTION

In today's highly competitive economy, a company's survival depends upon the marketing manager's ability to make sound business decisions, to outguess competitors, to anticipate consumer needs, to forecast business conditions and to plan generally for company growth. Marketing research is a tool used to accomplish these tasks. Such research is also vital in order to effectively monitor and evaluate past business decisions. A productive and thriving business will be one which suits the interests of customers, thus effective marketing begins with the recognition of customer needs.

It is well established that most communication occurs nonverbally (Weisner, 1988; Knapp, 1981; Seiter, 1987). That is, people "say" and "hear" a great deal more through nonverbal rather than verbal means of communication. However, virtually all market research tools rely on verbal means of communication such as questionnaires, telephone interviews, face-to-face interviews and discussions or focus groups. Such market research tools do not measure thought processes which are occurring without or below awareness. Indeed, even processes which the customer is aware of are often not measured well due to misreporting or under reporting for a variety of reasons.

Because companies rely so much on verbally oriented research tools they often miss much of what customers "say" and "hear" nonverbally. Thus, companies often miss important opportunities to understand customers better and to communicate better with them. As a consequence, companies miss opportunities to better serve their customers.

Similar to the situation of a company miscommunicating with its customers, communication within a company can be poor. This can be particularly true when the communication concerns thoughts and feelings about various personnel issues such as diversity, compensation, proposed or existing organizational arrangements such as merging and dividing debts, creating new organizational structures, interactions between superiors and subordinates and so on.

Lastly, self communication can also be an important issue; that is, how does the manager or C.E.O. think their customers think. These pre-existing biases can serve to "color" interpretations of marketing data. With awareness of these perceptions, one may more appropriately conduct market research.

A means for bringing to a level of conscious awareness those thoughts and feelings that are ordinarily not evident or are not evident in a clear or precise way is disclosed in U.S. Pat. No. 5,436,830 to Zaltman. Zaltman discloses a Metaphor Elicitation Technique which utilizes various research techniques to create a visually and other sensory oriented method and apparatus for creating research for marketing campaigns or to validate the thrust of an existing marketing campaign to determine if it accomplishes its stated purpose, this technique can also be used to improve inter-office and self communication. The disclosure of U.S. Pat. No. 5,436,830 to Zaltman is herein incorporated by reference in its entirety.

The process and apparatus of MET is based on the establishment of metaphors by users. A metaphor is the understanding and experiencing of one thing in terms of another. For example, a person may see a picture of an American flag as reflecting a sense of patriotism and hence be representative of his or her commitment to an American auto manufacturer.

The MET technique engages internal images, (neural patterns which underlie thought and feeling) and external images, (pictures, sounds, tastes, etc.) which represent or convey internal states of mind. It does this through a variety of steps and processes at each step. All sensory images are important nonverbal means of communication. Multiple sensory images are also important in the present invention since one sensory image such as sight can trigger the experience of another sensory image such as taste. This kind of connection among senses is known technically as synesthesia.

One outcome of the MET technique is a set of stimuli such as concepts or ideas which express important feelings and thought in the form of metaphors, among other things. These metaphors draw on all sensory perceptual systems, but especially vision since two-thirds of all stimuli reaching the brain do so through the visual system.

These concepts or ideas can then be used to develop a consensus map which is a diagrammatic metaphor for representing and understanding the preferences, opinions, and feelings of the user. It describes the thinking of a particular group of users such as customers, office personnel, or management, by synthesizing the mental models of individuals into an overall diagrammatic metaphor. It is, in fact, the major end product of the MET apparatus and process and is the guide to marketing staffs in the creation of advertising campaigns or formulating other marketing decisions and actions, to administrators in dealing with various personnel issues or to managers in unveiling pre-existing biases or beliefs.

Thus the MET technique and its apparatus is unique in how it engages the neural processes of thought and feeling and allows their expression in the form of metaphoric images which engage visual and nonvisual sensory systems.

The MET comprises the following steps:

Step 1. Storytelling. The user describes the content of relevant visual images and how they are associated with the research topic for that user. The images selected for the baseline series of images for evaluation for a topic under study.

Step 2. Sorting Task. The user sorts images into meaningful groups.

Step 3. Identifying and Recording Sensory Metaphors. The user identifies what is and what is not a good sensory representation of the research topic, in terms of sound, shape, tactile sensation, color, taste, smell or scent, and emotional feeling.

Step 4. Further Construct Elicitation. A formal interviewing process in which pictures and other sensory stimuli are used to understand user thinking about the research topic. The constructs elicited in this step augment those elicited in Steps 1–3.

Step 5. Most Representative Image. The user indicates which picture (from a given set of pictures) is most representative of the research topic (e.g., the meaning of luxury).

Step 6. Verbal Description of Missing Images. The user describes relevant pictures that he or she was unable to find or obtain and explains their relevance.

Step 7. Identifying Opposite Images. The user identifies pictures that describe the opposite of the topic (e.g., what is not luxury).

Step 8. Company Perceptions of Users. Using sensory metaphors, the user describes what a company and/or key people, e.g. car designers, sales personnel, etc. think of them. (This is important since a user's response to a company is also influenced by this perception.)

Step 9. Critical Message to the Company. The user describes the single most important message they want to convey to a company on the research topic. The user selects the sensory images that best reflect this message.

Step 10. Surprise to the Company. The user describes which of his or her feelings or thoughts on the topic a relevant company is least prepared to hear. The user selects the sensory images that best convey this information.

Step 11. The Mental Map. The user creates a map or a causal model using the constructs which have been elicited to express the user's overall thing about the research topic.

Step 12. Creation of a Summary Image. The user with the aid of a technician creates a single, still image (visual) which best summarizes the meaning of the research topic.

Step 13. Creation of a Vignette or Mental Video. The user, with the aid of a technician creates a movie-like vignette or video expressive of the research topic. This is done using animation. (Note: Steps 12 and 13 typically provide different but complementary information)

Step 14. Creation of the Consensus Map. The diagrammatic metaphor representing the researcher's understanding of user thinking. It consists of the users' most important constructs and their interrelationships. It describes most of the thinking of most users. It is an integration of information provided by all users participating in a project. Special analytic techniques are employed with the data used to construct the consensus map to determine whether market segments or subclusters of users can be identified within the consensus map. Thus one submap within the consensus map may be especially descriptive of one subgroup of users and another submap especially descriptive of another group's thinking. This analysis enhances the value of the consensus map in developing a marketing campaign.

The MET Apparatus

In order to effectuate the steps of the MET an apparatus is provided whereby a researcher, in conjunction with each user participating in a given research project, obtains the information needed to create the ultimate consensus map. The apparatus comprises a file of digital images from which are selected a series of images used for the storytelling step (Step 1). The user is able to add images to this file.

A digital sound recording is made of the user's story telling. The MET apparatus appends the digital sound recording to the digital image. The (digital) voice recording contains what is technically called paralanguage. Paralanguage consists of tone, inflection, and other cues or factors relating to how something is said. These factors convey important meaning beyond the actual words used and may even contradict those words. Paralanguage is generally considered a nonverbal dimension of communication.

The Sorting Task (Step 2) is accomplished by designating and sorting the various images retrieved, again using automated means of designating the images into different groups. For example, a user can "designate" which pictures fit into a particular group or group designation via a cursor or other keyboard input means.

The Sensory Metaphor step (Step 3) can also be accomplished via the apparatus whereby a user selects from a file or bank of sensory images those that are most expressive of the topic. These sensory images are stored digitally and represent an array of sounds, colors, shapes, and descriptions of smells, touches, etc. The user is able to add descriptions to this digital file. These images are metaphors. A digital sound recording is made of the user's description/ selection of these images.

Step 1, 2, and 3 identify some important user constructs. Additional constructs are also elicited (Step 4) using a specific interviewing procedure. The sensory images or metaphors the user has identified in steps 1, 2, and 3 are used as the stimuli for this conversation. The MET apparatus contains these images as well as a procedure for conducting the conversation. This procedure involves a set of specifically designed thinking probes to help the user express their feelings, thoughts, and values.

The Most Representative Picture (Step 5) is also designated via the pointing/selection apparatus of the present invention.

Verbal descriptions of relevant images (Step 6) not available at the time of the interview are provided by a user. Verbal records of these images are stored in the system. These images comprise scenes/pictures designated by the user as providing additional information about the topic under study.

Opposite Images (Step 7) are also presented to or selected by a user based upon the user's statements. These images are stored on a separate database of digital images.

The user describes how he or she thinks a company involved with the research topic thinks of them (Step 8). Users may feel that they are thought of in negative or positive ways. Users select sensory images (visual, tactile, sound, etc.) from the image file or bank which they believe reflect how a company thinks of them. The user's voice (audio) is recorded digitally on the apparatus of the present invention as he or she provides this information and is connected to the appropriate image.

The critical message to the company (Step 9) and the surprise to the company (Step 10) are illustrated by the user using various visual and other sensory metaphors in the image file or bank. The user's verbal commentary is recorded digitally (in audio) by the apparatus and connected to the appropriate images.

The Mental Map (Step 11) is a series of recorded constructs or images created by the user and stored in the system. These mental maps constitute accurate representations of ideas important to the user and how they relate to one another. The set of constructs elicited through earlier steps are brought up on the display device of the apparatus. These are validated by the user. The user then establishes connections among the constructs using a mouse, cursor, or pressure sensitive digitizing tablet (using a stylus or even a finger.)

A composite or summary digital image is created next (Step 12) using a form of "clip art" common to many desk top publishing systems and an image management system stored in the CPU. A technician assists the user in the use of the software. A user's own pictures often form the starting point for this step. A digital voice recording is made of the user's explanation of this summary image and is appended to the image as part of the record.

The user's description of a movie-like vignette (Step 13) describing the research topic is recorded. That is, the user's voice is digitally recorded (as in earlier steps) as this vignette is described. The user then directs a technician in the creation of an animated representation of this vignette using standard computer video animation techniques. The user's digitally recorded (audio) description is appended to this vignette.

The final creation of a consensus map (Step 14) is essentially the summation of all of the data created by individual users using the apparatus. The consensus map contains verbal labels for each major construct. Constructs that are related to one another are connected with arrows. The researcher or marketing manager is able to click (with a mouse or other device) on a particular construct. When this is done the most relevant pictures and other sensory metaphors associated with that construct appear on the computer screen or other display device. Where appropriate, the digitally recorded voices of users commenting on the pictures or other sensory metaphors are also presented. The researcher or marketing manager may also click on an arrow connecting any two constructs and retrieve a verbatim text and/or audio statement from one or more users describing how one construct affects the other.

The researcher or marketing manager is also able to review all animated vignettes created in Step 13. These vignettes are indexed to constructs in the consensus map and to their interrelationships. Thus, it is possible to see and hear an animated enactment of a construct and its impact on other constructs.

The metaphors associated or connected with each construct are the sensory definitions of those constructs. They convey the important nonverbal meanings of these constructs. It is these meanings which are often missing from market research. This is partially due to the fact that verbal skills of those whose input is being solicited vary widely. It has been found however that in employing the MET, the verbal skills of a user are not critical since the visual sensory development of persons is relatively more advanced than verbal development. Therefore, education level and/or age of a user is not critical to the MET. Generally users using the MET are more equal on a sensory level than they are on a verbal skills level. This in turn contributes to the accuracy and consisting of responses generated.

The MET presently runs on the Apple Mackintosh family of computers. However, the MET can also be implemented on IBM and IBM compatible computers employing the Intel® 80386, 80486 family of processors. Input scanners such as the Apple OneScanner Polaroid CS-5000Photo Print Scanner, the Microtek ScanMaker 1850S (35 mm slide/negative scanner) and the Microtek ScanMaker 6007S flatbed scanner are all appropriate scanners for use with the present invention.

Other input devices include the WACOM SD420E Digitizing Tablet for shape input and the delineate portions of images to be extracted as well as the CALCOMP Drawing Board Roman II Digitizing Table for the same purpose.

Additional output devices include the LaserMaster 1000 and the GSC ColorFast Digital Film Recorder for providing hard-copy output of images created.

It is desirable to further refine the information obtained through practicing the MET technique. That is, once the key constructs and important metaphors have been identified, it is useful to assess them further. For example, what is their relative importance? Do they produce responses that people may have trouble articulating orally or using paper and pencil measures such as questionaires? Do they produce responses that people are not aware they are experiencing? Are some of these constructs and metaphors more memorable than others? Are some more positive (negative) than others? This refinement is the subject matter of the present invention.

SUMMARY OF THE INVENTION

It is therefore an object of the present invention to provide a method for augmenting the Metaphor Elicitation Technique by using techniques that monitor physiological functioning.

It is a further object of the present invention to monitor physiological functioning through the use of functional magnetic resonance imaging, positron emission tomography, galvanic skin response or conductance, event related potentials, or heart rate changes.

It is a further object of the present invention to monitor the brain activities which underlie uncovered thoughts.

It is a further object of the present invention to monitor brain blood flow as a function of marketing related stimuli.

It is yet a further object of the present invention to monitor brain blood flow through either the use of positron emission tomography (PET scans) or functional magnetic resonance imaging (fMRI).

DETAILED DESCRIPTION OF THE PREFERRED EMBODIMENT

Figure 1:
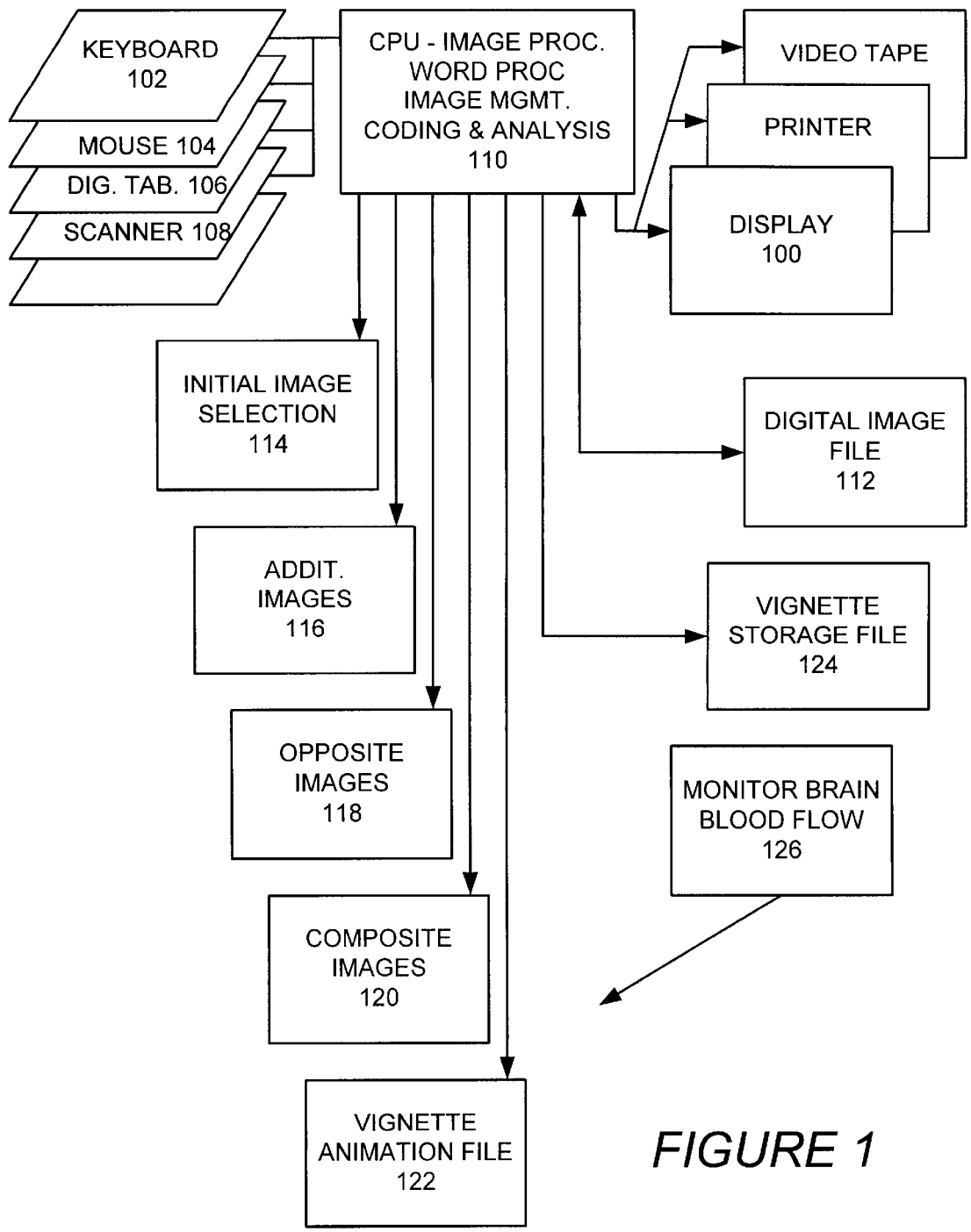
FIG. 1—System architecture

Referring to FIG. 1 the MET apparatus is described. The apparatus comprises display 100 for displaying alpha numeric data as well as the various images viewed by a user. The apparatus further comprises keyboard 102, mouse 104, pressure sensitive digital tablet 106, and scanner 108, for reading slides, negatives, and pictures into Central Processing Unit (CPU) 110 for inputting data and designating images or sections of images which are to be used in the creation of composite images or to merely designate those images to be stored.

CPU 110 comprises various logic whereby input commands can be received from keyboard 102, mouse 104, and pressure sensitive digitizer tablet 106 to designate various images for subsequent processing and storage. CPU 110 comprises image processing/management software for cutting and pasting portions of images from one into another as well as to allow the input of alpha numeric data. CPU 110 also comprises file management software allowing digital images to be received, displayed and stored. It also comprises file management software for computer animation. CPU 110 also contains software for coding and analyzing constructs, sensory metaphors, still images, vignettes, and certain aspects of users' verbal language digitally recorded or entered by the researcher as written text. CPU 110 contains additional software that creates tables, graphs, consensus maps, and other analyses unique to MET and required for reporting research results. CPU 110 also contains software which helps guide the researcher and users through the sequence of steps and through the activities within each step.

Digital image file 112 comprises a large library of digital images from which are selected images for the initial groupings and subsequent images as required for a user during the course of any given study. This file includes visual images as well as those relating to the several other senses (Step 3).

The MET system also comprises a series of temporary storage files in which are stored initial images 114 selected for evaluation, additional images 116 selected by a user for use in the verbal image (Step 6), opposite images 118 for use in the description of those images which are opposite to the concept being evaluated (Step 7), composite image file 120 in which is stored the digital image created by the user (Step 12), vignette animation file 122 comprising parts of all other images selected and temporarily stored as a file of images for use in the creation of a vignette (Step 13), and vignette storage file 124 for storing complete vignettes.

During Step 1, the user is asked to describe the salient contents of each picture displayed. These salient or relevant characteristics are stored. The pictures are presented to the user during Step 1, on the video display of the present invention. During this and other stages, the user's verbal comments are audio recorded digitally, in the computer control processor.

During Step 2, the user is asked to sort the pictures into meaningful categories and provide a label or description for each category. There are no restrictions as to the number of categories or the number of pictures in each category. This sorting task helps establish the major themes or constructs relevant to a particular user. In addition, the sorting task is used as a precursor to Step 4, the further elicitation of constructs using probing interviewing.

In Step 3, the user is asked to describe what are and what are not good sensory representations of the research topic. For example, people often use their senses to describe their experiences, thoughts or emotions. Thus, this step elicits from a user what is and is not the taste, touch, smell, color, and sound of the concept being explored. In addition, the emotional feeling associated with the topic is also elicited. These sensory thoughts are recorded by the present invention during this step of the process.

In Step 4, the user is engaged in a discussion with the researcher which results in the elicitation of additional relevant constructs. The stimuli used for the elicitation of additional constructs are the pictures, picture groupings, and other sensory images identified and selected in steps 1 through 3. The elicitation of constructs is facilitated by the use of probing interviewing techniques designed for MET.

In Step 5, the most representative picture is selected from the group of pictures initially provided by the present invention during Step 1 and augmented by pictures the user brings to the researcher. The picture selected is that which is most expressive or representative of the assigned topic. It is important to note that this picture is often used as a starting point for the summary image of Step 12 (to be discussed below).

During Step 6, other images are recalled from the memory of stored images of the present invention. These pictures are those which are deemed relevant by the user to the topic being described. This step is critical since the pictures originally shown to the user may not be those most appropriate given that user's background and perception. Also, pictures the user wanted to bring to the meeting with the researcher may not have been available to the user. These additional images are also relevant to the Step 12 development of the summary image.

During Step 7, opposite images are selected by a user. Research has shown that any concept or construct contains a reference also to its opposite meaning (Brunette and Wills, 1989). The user is thus asked to retrieve pictures that might describe the opposite of the topic being studied. For example, if the original assignment concerned the meaning of "coffee as a morning wakeup beverage," the user is asked what pictures would not reflect the concept of coffee as a morning wake up beverage. Such pictures are selected from the file of stored images in the present invention and subsequently stored as a response of that particular user.

Step 8 provides the user an opportunity to describe how he or she thinks the companies involved with a certain product think of their users. The user illustrates these thoughts with images from the present invention. Market research tools are almost always focused on eliciting what users' think of a product, brand, or company. While this is important, a person's response to a service provider or to a product also depends on how they feel they are perceived. Thus, how a user or patient believes an HMO's physicians or other staff think of them will influence that person's decision to use that HMO and, if they join, will also influence their use of medical services.

Step 9 enables the user to identify the most important thought they have which they feel a company should understand. The sensory images associated with the thought are selected by the user (from within the apparatus) to help convey their thinking.

Step 10 identifies information that the user thinks will be surprising to a company, i.e. information that the user thinks the company is least prepared to hear. This provides additional perspective about how well informed users feel companies are about their needs. Here, too, users' thinking is clarified by the use of sensory images drawn from the present invention.

Step 11 is the creation of a mental map or model involving the constructs of the person viewing the pictures. The user reviews all of the constructs recorded by the present invention and verifies that they are accurate or whether there are important ideas missing from the list of constructs. These constructs are then graphically linked to one another based upon relationships established by the user and stored by the system. This forms the mental model, or the mental map. This map is entered into the central processor unit. The user provides a brief description of the map which is audio recorded digitally in the computer.

After completing the mental map, the user creates a summary image or digital montage which expresses the topic under study (Step 12). This is done using the images already selected together with the graphical ability of the present invention to combine images or portions of images to create a single summary image. All of the pictures selected by a particular user are stored in the computer. Additional images are also available from the stored file of images of the present invention. During this step the user can use one picture as a background for the new image and add elements from other pictures and augment these with new art work. Using image processing and manipulation techniques, the user can rearrange and alter the subject, the foreground, the background, or specific elements including color, object size, shapes, positions, and even textures appearing within an image to be more expressive of the concept under study. For example, a person dressed in a particular way may be expressive of a particular automobile concept. Such a person captured in one photograph can be "cut" moved to a clip board, resized, placed at a different angle, and have the color of clothing changed, and then "pasted" electronically onto another picture containing other meaningful information.

The "cut-out" image could also come from a tool box or collection of pictures maintained in the separate image file. The user's description of the significance of this image is audio digital recorded and made a part of the picture file. This image can also be printed or recorded on film to create a hard copy record of the picture created.

After completing the summary still image (Step 12) the user next describes a movie-like vignette or video in which action or motion is involved (Step 13). Thus a user describing coffee as a morning wake-up beverage may describe someone in a farm setting, walking to the road to get the newspaper from a mail box, the sun rising, a rooster crowing in the background, and the same person returning to enter a kitchen where a mug of steaming hot coffee is waiting. This vignette is readily created using computer animation techniques and may require less than one minute to play when completed. The user's description of the significance of this vignette is audio recorded digitally and made part of the vignette.

The information provided by steps 12 and 13 complement one another and often produces new constructs and/or new insights about previously identified constructs.

The final step in the process (Step 14) is the creation of the consensus map by the researcher. The images and constructs elicited during use of the present invention, the development of each user's mental model, and the digitized images created provide the data base from which the consensus map is generated. The consensus map describes a) most of the thinking of, b) most of the people, c) most of the time. Thus the data from all users are aggregated and developed into a consensus map.

This consensus map contains the most important set of constructs that influences user perception, understanding and behavior. These constructs are then used to guide the development and implementation of a marketing campaign for a particular product.

Figure 2:
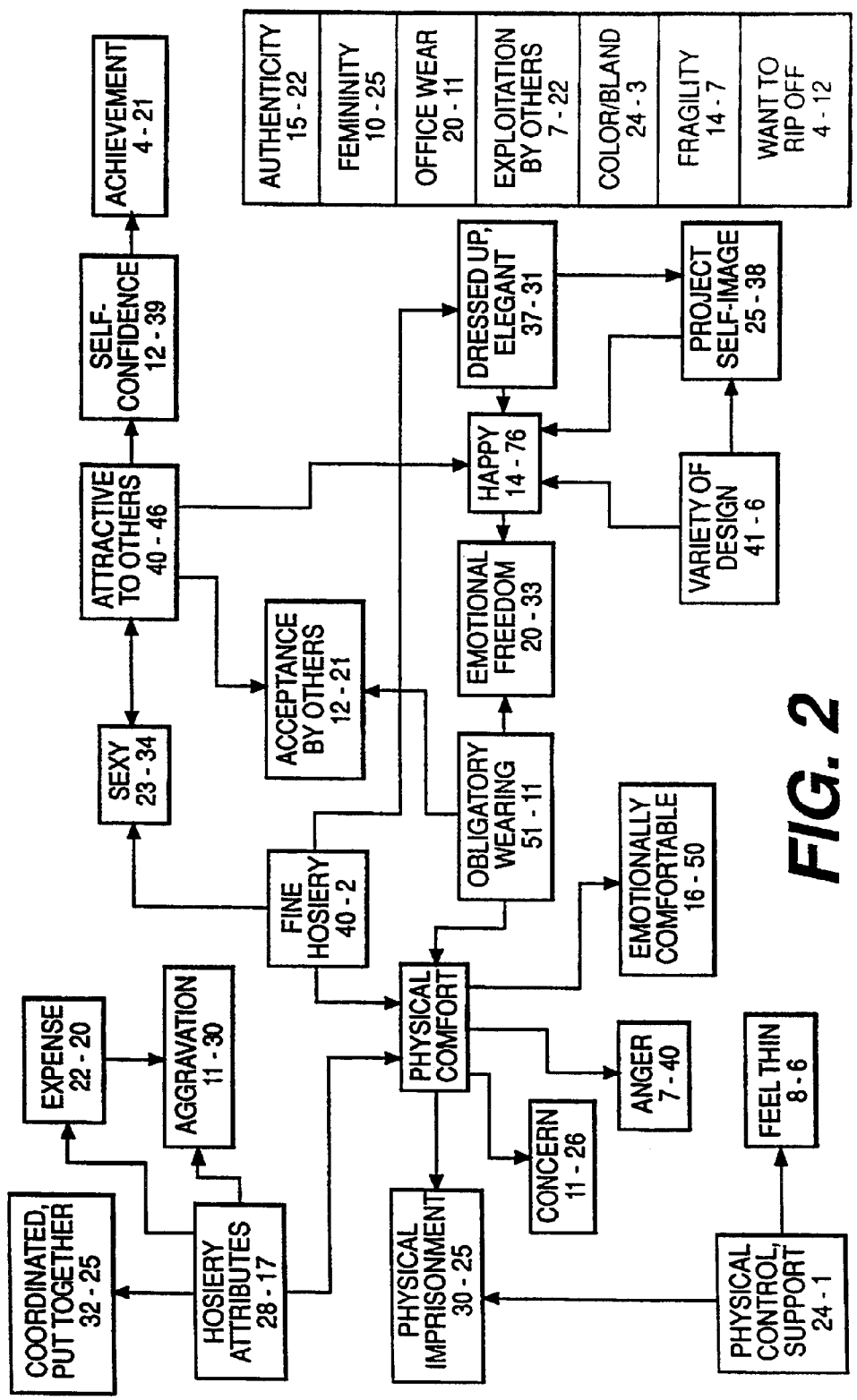
FIG. 2—Consensus map example: Hosiery wearing experience

FIG. 2 shows an example of a consensus map. In this example, the subject product was hosiery. Various constructs directed toward the hosiery were elicited from the participating subjects. Some construct examples shown in the figure are self-confidence, emotional freedom, and aggravation. In all, thirty different constructs were mentioned by at least ten of the 25 subjects. Sometimes a subject noted a relationship between two or more of the constructs she mentioned. For example, some subjects linked the construct of self-confidence to the construct of achievement, meaning that in her mind, these distinct attributes were related.

Of the thirty constructs mentioned by at least ten of the subjects, 23 were mentioned at least five times as being related to another construct. The 23 constructs are shown drawn within ovals in FIG. 2. Arrows are shown drawn between these ovals. The oval from which the arrow originates contains the construct which is the origination point in that construct's relationship with the construct resident in the oval upon which the arrow terminates. The originating construct is the attribute which the subject felt was the cause of the second construct. For example, some women thought that the construct of expense involved in wearing hosiery led to a construct of aggravation. In some cases, the arrow points in both directions between constructs.

Beneath each construct are two numbers separated by a hyphen. The number to the left of the hyphen indicates the number of times this construct was the origination point in the relationship with another construct. The number to the right of the hyphen indicates the number of times this construct was the destination point in a relationship with another construct.

The seven constructs listed in the rectangular box on the right side of FIG. 2 complete the original thirty constructs that were mentioned by ten or more of the 25 subjects.

How to Use

When a particular study is to be done concerning a topic, the market researcher initially selects a series of images for a user to view. These images include those a user brings to the meeting. This initial story telling (Step 1) provides basic images that describe the concept being evaluated.

The user next sorts the images by designating on the display screen which images fall into a user defined series of groups. This sorting task (Step 2) is done with the aid of a cursor, mouse or a stylus using a pressure sensitive digitizer tablet. The activated cursor selects the image.

During the sensory metaphor step (Step 3) the user again uses the cursor, mouse or pen-like stylus to identify what are and are not good sensory representations of the research topic. Again, the user may augment the existing file of sensory representation with their own sensory definitions.

During Step 4, the three visual images are selected randomly and their similarities and differences are explored using special techniques. The interviewing technique probes for basic meanings and connection to the research topic. The selection of groups of three images continues until the various associations amongst the images are defined.

During Step 5, the user again through use of a cursor mouse or stylus pen indicates which is the most representative picture of the research topic.

Thereafter during Step 6, the user is allowed to retrieve additional digital images from digital image file 112 which may not have been in the original group of images displayed to the user. The relevance of these images is then recorded via alpha numeric input.

The user is next directed by the apparatus during Step 7 to retrieve images which describe the opposite of the topic being studied. These images are retrieved and appropriately stored.

During steps 8, 9, and 10 the user describes how they believe companies think of them (step 8), what the most important thought is they would like to convey to companies involved with the product or service being studied (step 9), and what they believe these companies would be most surprised to learn about their user's thinking (step 10). Sensory images associated with this information are selected or described by the user. These images are appropriately stored. The user's descriptive comments about these sensory images are also recorded using digital audio. Thus during a play back, the sensory image is brought to a display screen and the user's voice is heard describing the relevance of that image.

During Step 11, the user creates a graphical model of his or her thinking using the various constructs which have been elicited during the course of the analysis. This is accomplished via graphical and image programs stored in the CPU.

During Step 12, a summary digital image is created whereby a user can cut and paste various portions of the different images collected into a montage or summary image depicting the concept being studied.

During Step 13, a movie-like vignette is created whereby the user is able to create an animated representation of their thinking. Standard procedures are available to accomplish this. The animation is stored in the CPU along with an audio description of the animation provided by the user.

Finally, during Step 14 the apparatus is used to diagrammatically represent the understanding among users of the concept being studied and the relevance of the images revealed during the course of that study. From this information an approach to a marketing activity is then derived. The apparatus of this invention connects each verbal construct in the consensus map with representative visual and other sensory images. This provides marketing managers with far richer data than do other techniques and thus permits more effective marketing programs.

As mentioned, the techniques described in this specification are not limited to marketing analysis. For example, the field of social network analysis is also amenable to the application of the techniques described herein. Instead of visual metaphors for products, visual metaphors for people, organizations and positions within organizations would be elicited from users. The output, or consensus map, would depict the various constructs and relationships among them as they relate to organizational or social network structure. These in turn would describe the strength of relationships and the attributes of particular individuals or groups of individuals within an organization. In the case of a vacant position, the user would visually describe the attributes of the ideal person needed to fill such a position to name but a few such applications of the MET.

MET Monitoring

By monitoring the physiological functions of the user, further insight can be obtained regarding the topic under consideration. Monitoring techniques can include functional magnetic resonance imaging, positron emission tomography, galvanic skin response or conductance, event related potentials or heart rate changes. From brain imaging measurements 126, inferences can be made about the function of specific regions of the human brain and how the integration of activity of geographically separate brain structures facilitates the psychological process under study. Evidence indicates that the brain is composed of a series of function-specific substructures. The organization within and between these substructures facilitates the spectrum of perceptual, cognitive and behavior production capacities accessible to an animal. A given psychological process such as forming a mental image, recalling a memory, solving a reasoning problem or generating an emotional response, requires increased or decreased processing within specific subsets of brain regions. Where there is increased processing within a brain region there must be a proportional increase in the concentration of oxygen and other blood-born metabolites accessible to that brain region. Thus, measuring the concentration of blood flow to the brain while an individual performs an isolated cognitive task provides a means of measuring the relative processing contribution of each subregion to the task.

In this fashion, the occurrence of unconscious processes—mental states involving feelings and thoughts people are unaware of—can be observed using techniques that monitor blood flow and other activity in various parts of the brain. For example, we know that when people are listening to a voice describing an automobile dealership, there is increased blood flow in the primary and secondary visual areas of their brain. This indicates that they are visualizing the dealership setting even if they may not recall that they are doing so. Additionally, when a positive description—based on the metaphor elicitation technique—is read to them the left dorsolateral prefrontal cortex is especially active, along with the cognitive functions associated with that area of the brain. When a negative description is read—again based on what is learned from MET—the right dorsolateral prefrontal cortex is especially active along with the cognitive functions associated with that area of the brain. Research has shown an association between the following: the superior temporal gyrus and the processing of sounds; the posterior cingulate and fixating attention to a stimulus; area 19 and associative memory; inferior temporal and recognition; parahippocampal and memory; precuneus and spatial mental imagery; insula and negative emotional associations; area 17 and visual processing; and areas 18 and 19 and processing images generated during visual mental imagery.

Several means for monitoring brain activity are known to those skilled in the art. One such means is positron emission tomography (PET). PET is the tomographic imaging of local metabolic and physiologic functions in tissues, the image being formed by computer synthesis of data transmitted by positron-emitting radio nuclides, often incorporated into natural biochemical substances and administered to the patient. A computer traces the path of photons and produces a composite image representing the metabolism level of the biochemicals in the tissue.

In practice, during a PET scan, the subject inhales a trace amount of radioactive oxygen wile he or she is engaged in the psychological task. The radioactive oxygen binds to a protein in the blood, such as hemoglobin, and passes through the circulatory system, and up into the brain. The PET scanner is equipped with a series of radiation detectors which quantify the level of radiation in a 3-D space. After the scan is completed the information from the PET scanner is analyzed by a program which maps the region-specific levels of radiation onto the topology of the brain. The result is an image of the brain that depicts the differential blood flow during the performance of the task and a set of statistical values that indicate the significance of the blood flow to each region.

A second exemplary means of brain monitoring is functional magnetic resonance imaging or fMRI. FMRI is a diagnostic modality, using nuclear magnetic resonance technology, in which the patient's body is placed in a magnetic field and its nuclei (hydrogen) are excited by radio-frequency pulses at angles to the field's axis; resulting signals from the hydrogen ions, varying in strength where hydrogen is in greater or lesser concentrations in the body, are processed through a computer to produce an image. By varying the radio-frequency pulse sequences, the apparent contrast of adjacent tissues and of black and white values can be altered.

In practice, a person creates a digital image summarizing their key thoughts and feelings using the metaphor elicitation technique as described above, the person is then placed in a device which monitors physiological functioning. In a preferred embodiment, brain activity is monitored, although skin response and heart rate can also be monitored. Where brain activity is to be monitored, the user is placed in PET scan or fMRI device.

The person then reads and/or views and describes again his or her digital image. As this external image about a product or service is engaged by the person, the brain activity monitoring device records differential activity in various parts of the brain. This process provides special insights about the relative importance of the ideas represented by the digital image based upon the cognitive functions performed by specific areas of the brain. In a preferred embodiment, the monitored brain activity is recorded electronically.

Software is required to capture and analyze this brain activity. This software is generally known to those skilled in the art and includes Statistical Parametric Mapping (SPM) as developed by Karl Friston and colleagues at Hammersmith Hospital in London, U.K. SPM software allows one to transform the images from the subject's brains to a normalized size and shape based on the coordinates of Talairach and Tournoux and then to contrast conditions by summing over the entire group of subjects and subtracting the sum of one condition from that of the other. The result is a color map where more intense colors, such as red and white, indicate stronger activations. The activations are measured by a Z-score associated with each pixel in the contrast image.

In alternative embodiments, monitoring the physiological functions of the user can take place throughout, or at any time during, the metaphor elicitation technique.

Although the method of the present invention has been described in detail for purpose of illustration, it is understood that such detail is solely for that purpose, and variations can be made therein by those skilled in the art without departing from the spirit and scope of the invention. The apparatus, operation and method of the present invention is defined by the following claims.

What is claimed is:

1. A process for eliciting, organizing and analyzing data pertaining to a research topic, comprising:
   establishing a series of base line images in a first file in computer memory relating to the research topic;
   sorting the baseline images into groups by a user, each of the groups having similar qualities;
   eliciting and storing sensory and emotional perceptions from the user regarding the research topic;
   eliciting and storing constructs and interrelationships from the user, regarding the research topic, using an interview procedure;
   eliciting and storing a baseline image from the user that correlates closest with the research topic;
   eliciting and storing additional images from the user that correlate closest with the research topic;
   eliciting and storing opposite images from the user that represent ideas opposite to ideas represented by the research topic;
   creating a user's composite digital image best depicting the research topic;
   monitoring the user's brain blood flow while the user reviews the composite digital image;
   electronically recording data related to the user's brain blood flow; and
   analyzing the data to determine user reaction to the composite digital image.

2. The process for eliciting, organizing and analyzing data pertaining to a research topic as in claim 1 wherein an additional physiological function is analyzed selected from the group consisting of heart response and skin response.

3. The process for eliciting, organizing and analyzing data pertaining to a research topic as in claim 1 wherein the user's brain blood flow is analyzed to determine the intensity of the user reaction.

4. The process for eliciting, organizing and analyzing data pertaining to a research topic as in claim 1 wherein location of the user's brain blood flow is analyzed to determine whether the user reaction is positive or negative.

5. The process for eliciting, organizing and analyzing data pertaining to a research topic as in claim 1 wherein the user's brain blood flow is monitored by a means selected from the group consisting of functional magnetic resonance imaging and positron emission tomography.

6. A process for eliciting, organizing and analyzing data pertaining to a research topic, comprising:
   establishing a series of base line images in a first file in computer memory relating to the research topic;
   monitoring a user's brain blood flow;
   electronically recording data related to the user's brain blood flow;
   sorting the baseline images into groups by a user, each of the groups having similar qualities;
   eliciting and storing sensory and emotional perceptions from the user regarding the research topic;
   eliciting and storing constructs and interrelationships from the user, regarding the research topic, using an interview procedure;
   eliciting and storing a baseline image from the user that correlates closest with the research topic;
   eliciting and storing additional images from the user that correlate closest with the research topic;
   eliciting and storing opposite images from the user that represent ideas opposite to ideas represented by the research; and
   creating a user's composite digital image best depicting the topic under study.

7. The process for eliciting, organizing and analyzing data pertaining to a research topic as in claim 6 further comprising:
   analyzing the user's brain blood flow data to determine user reaction to information selected from the group consisting of baseline image, sensory and emotional perceptions, constructs and interrelationships, additional images, opposite images, and composite digital image.

8. The process for eliciting, organizing and analyzing data pertaining to a research topic as in claim 6 wherein an additional physiological function is analyzed selected from the group consisting of heart response and skin response.

9. The process for eliciting, organizing and analyzing data pertaining to a research topic as in claim 7 wherein the user's brain blood flow is analyzed to determine the intensity of the user reaction.

10. The process for eliciting, organizing and analyzing data pertaining to a research topic as in claim 7 wherein location of the user's brain blood flow is analyzed to determine whether the user reaction is positive or negative.

11. The process for eliciting, organizing and analyzing data pertaining to a research topic as in claim 7 wherein the user's brain blood flow is analyzed by a means selected from the group consisting of functional magnetic resonance imaging and positron emission tomography.

12. A metaphor elicitation and physiological functioning monitoring apparatus comprising:
   a central processor comprising image processing logic to create and manipulate digital images selected for a research topic;
   a display device connected to the central processor to display the digital images;
   a first input device disposed to provide alphanumeric data to the central processor;
   a second input device disposed to manipulate a computer cursor visible on the display device and indicative of alphanumeric data placement;
   a third input device disposed to manipulate image data visible on the display device;
   baseline digital image memory disposed to store baseline digital images and to provide the baseline digital images to the central processor for manipulation and display;
   second digital image memory disposed to store additional digital images and to provide the additional digital images to the central processor for manipulation and display;

third digital image memory disposed to store opposite digital images and to provide the opposite digital images to the central processor for manipulation and display;

a means for monitoring brain blood flow to determine a user's reaction to information selected from the group consisting of baseline digital images, additional digital images, and opposite digital images;

a recording means for electronically recording data obtained through the means for monitoring brain blood flow; and a data analysis means for analyzing the electronically recorded data.

13. The metaphor elicitation and physiological functioning monitoring apparatus as in claim 12 wherein the central processor generates a graphical representation of relationships among the stored images and the central processor manipulates a plurality of graphical representations to derive a consensus map.

14. The metaphor elicitation and physiological functioning monitoring apparatus as in claim 12 wherein an additional physiological function is analyzed selected from the group consisting of heart response and skin response.

15. The metaphor elicitation and physiological functioning monitoring apparatus as in claim 13 wherein the means for monitoring brain blood flow to determine a user's reaction to information is selected from the group consisting of relationships among the stored images, and consensus map.

16. The metaphor elicitation and physiological functioning monitoring apparatus as in claim 15 wherein the user's brain blood flow is analyzed to determine the intensity of the user reaction.

17. The metaphor elicitation and physiological functioning monitoring apparatus as in claim 15 wherein location of the user's brain blood flow is analyzed to determine whether the user reaction is positive or negative.

18. The metaphor elicitation and physiological functioning monitoring apparatus as in claim 15 wherein the means for monitoring brain blood flow is selected from the group consisting of functional magnetic resonance imaging and positron emission tomography.

19. An improved marketing process of the type in which a metaphor elicitation technique is used, wherein the improvement comprises:

monitoring a user's brain blood flow wherein said monitoring takes place at time points selected from the group consisting of throughout the metaphor elicitation technique, at distinct time points during the metaphor elicitation technique or upon completion of the metaphor elicitation technique.

20. An improved marketing process of the type in which a metaphor elicitation technique is used, as claimed in claim 19, wherein the improvement further comprises:

electronically recording data related to the user's brain blood flow.

21. An improved marketing process of the type in which a metaphor elicitation technique is used, as claimed in claim 20, wherein the improvement further comprises:

analyzing brain blood flow data to determine user reaction to information acquired through the metaphor elicitation technique.

22. An improved marketing process of the type in which a metaphor elicitation technique is used, as claimed in claim 19, wherein an additional physiological function is analyzed selected from the group consisting of heart response and skin response.

* * * * *